United States Patent
Calafut

(10) Patent No.: US 6,488,574 B1
(45) Date of Patent: Dec. 3, 2002

(54) NAIL FILE WITH INDICIA AND MIRROR

(76) Inventor: Edward J. Calafut, 2590 Glen Wood Rd., Vestal, NY (US) 13850

( * ) Notice: Subject to any disclaimer, the term of this patent is extended or adjusted under 35 U.S.C. 154(b) by 0 days.

(21) Appl. No.: 09/551,857

(22) Filed: Apr. 18, 2000

Related U.S. Application Data

(63) Continuation-in-part of application No. 09/045,957, filed on Mar. 23, 1998, now Pat. No. 6,062,967.

(51) Int. Cl.[7] .......................... B23D 71/04; A45D 29/04
(52) U.S. Cl. ......................... 451/523; 451/533; 132/73; 132/76.4
(58) Field of Search ................................ 451/523, 533; 132/73, 75.6, 76.4

(56) References Cited

U.S. PATENT DOCUMENTS

| | | | |
|---|---|---|---|
| 2,557,175 A | * | 6/1951 | Cortes ........................ 132/76.4 |
| 2,699,791 A | * | 1/1955 | Hansen ....................... 132/76.4 |
| 3,656,265 A | * | 4/1972 | Schaffner, Jr. ................. 51/295 |
| 4,336,815 A | * | 6/1982 | Ross ........................... 132/143 |
| 4,457,987 A | | 7/1984 | Pangburn |
| 4,534,138 A | | 8/1985 | Pangburn |
| 4,712,552 A | * | 12/1987 | Pangburn .................... 128/355 |
| 4,911,734 A | * | 3/1990 | Short ............................ 8/471 |
| 4,927,483 A | | 5/1990 | Bray |
| 5,036,561 A | | 8/1991 | Calafut |
| 5,109,637 A | | 5/1992 | Calafut |
| 5,361,786 A | * | 11/1994 | Pangburn .................... 132/200 |
| 5,567,520 A | | 10/1996 | Neckermann |
| 5,658,184 A | * | 8/1997 | Hoopman et al. ............. 451/28 |
| 5,666,981 A | | 9/1997 | Stephens |
| 6,062,967 A | * | 5/2000 | Calafut et al. .............. 451/523 |
| 6,145,512 A | * | 11/2000 | Daley ........................ 132/76.4 |

* cited by examiner

*Primary Examiner*—Daniel C. Crane
*Assistant Examiner*—William Hong
(74) *Attorney, Agent, or Firm*—Siemens Patent Services

(57) ABSTRACT

A slightly bendable nail file which has indicia in the form of a pictorial image. The file comprises a flexible foamed synthetic resin core sandwiched by paperboard panels. Each paperboard panel has a layer of transparent grit bonded thereto. One paperboard panel has a photograph formed thereon, the photograph being outwardly visible through the transparent grit. The other paperboard panel has a mirror coating.

8 Claims, 2 Drawing Sheets

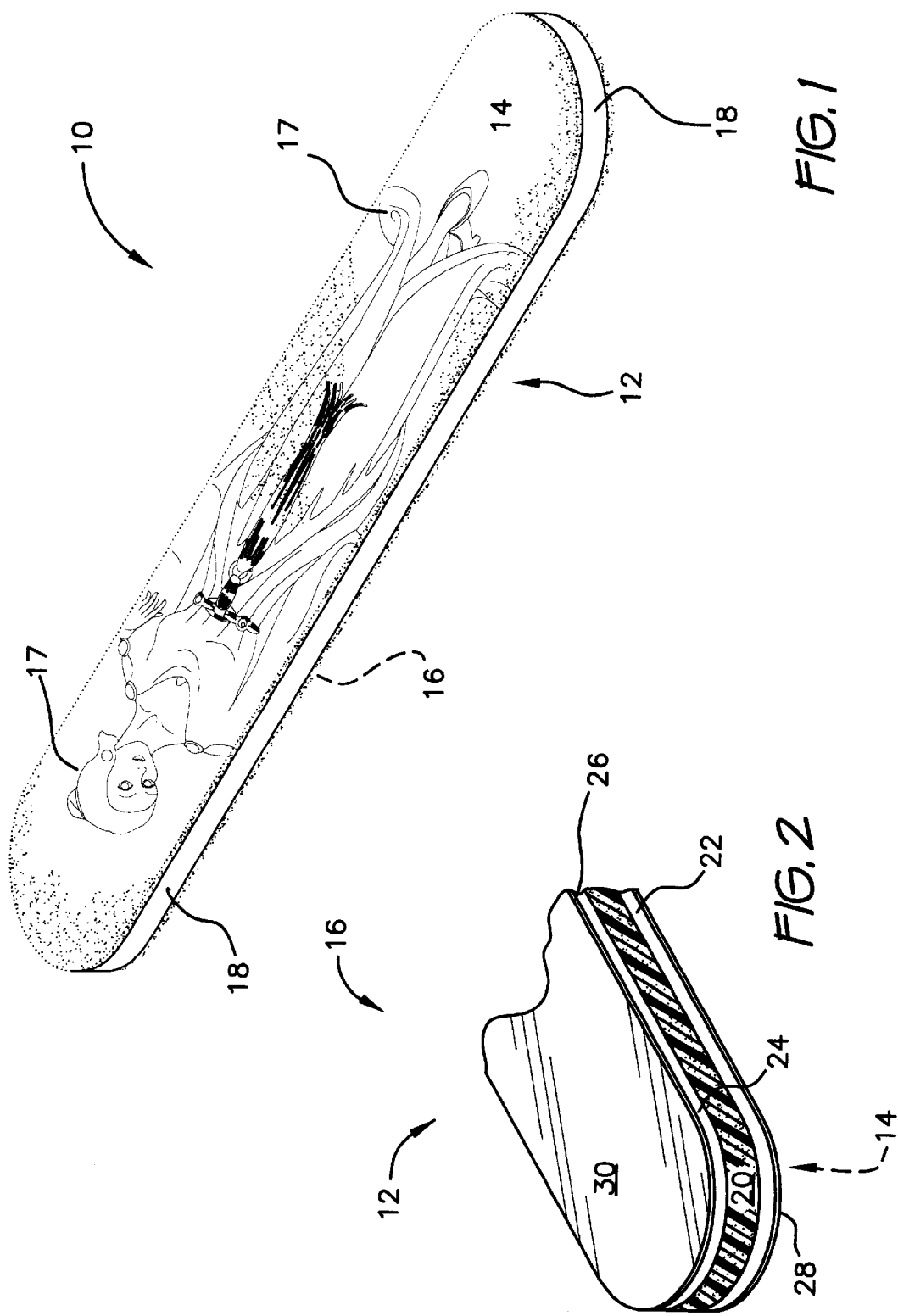

NAIL FILE WITH INDICIA AND MIRROR

REFERENCE TO RELATED APPLICATION

This application is a Continuation-In-Part of Ser. No. 09/045,957, filed Mar. 23, 1998 now U.S. Pat. No. 6,062,967.

BACKGROUND OF THE INVENTION

1. Field of the Invention

The present invention relates to flat, hand held files of the type generally employed for abrading finger nails and the like. More particularly, the invention comprises a file having indicia disposed thereon, with transparent grit or abrasive disposed over the indicia, with a mirrored opposing surface. The indicia is revealed through the transparent grit. The nail may be employed in conventional fashion while displaying the indicia without obstruction from the grit both in its original condition and after it has been employed for abrading. The mirrored surface provides a convenient second cosmetic function which would otherwise require a separate apparatus. The invention is useful both in professional and consumer applications wherever cosmetic products and procedures are utilized.

2. Description of the Prior Art

Finger nail files are generally purely utilitarian devices intended for abrading finger nails. They generally comprise planar members having a rough surface suitable for abrading finger nails. Finger nail files are generally fabricated in one of two ways. The file may be formed from a stratum of metal, such as steel, which is scored or otherwise treated to have a roughened or abrasive surface.

While steel files are durable, they lack flexibility. Flexibility imparts an ability to conform to a body surface. Conformity enables a more even polishing to be achieved. Flexible finger nail files have been provided in the prior art by forming the file from parallel strata including a flexible core stratum and surrounding strata fabricated from materials suitable for carrying abrasive in the form of grit of predetermined fineness.

Flexible nail files or similar implements are seen in U.S. Pat. Nos. 4,459,987 and 4,534,138, issued to William E. Pangburn respectively on Jul. 17, 1984, and Aug. 13, 1985, U.S. Pat. No. 4,927,483, issued to David Bray on May 22, 1990, and U.S. Pat. No. 5,666,981, issued to Dallas H. Stephens on Sep. 16, 1997, as well as in my prior U.S. Pat. No. 5,036,561, issued Aug. 6, 1991, and U.S. Pat. No. 5,109,637, issued May 5, 1992. U.S. Pat. No. 5,567,520, issued to Edwin F. Neckermann on Oct. 22, 1996, describes translucent or transparent grit. However, none of these patents shows or suggests use of indicia on a nail file, much less indicia revealed in or behind transparent or translucent grit, or incorporating a mirror into a nail file, these being characteristics of the present invention.

None of the above inventions and patents, taken either singly or in combination, is seen to describe the instant invention as claimed.

SUMMARY OF THE INVENTION

The present invention provides a nail file displaying indicia on at least one broad face. In a preferred embodiment, the face displaying indicia also bears abrasive grit. The grit is transparent or translucent, so as to reveal the indicia below. The face of the nail file therefore performs two functions, those of displaying indicia and also bearing a roughened surface for abrading. The file also incorporates a mirror on the side opposite that bearing abrasive grit. This feature enables consumers and cosmetologists to perform two cosmetic functions utilizing one apparatus.

Indicia may take any form, such as a pictorial image or imprinted data. The data may convey messages relating to advertising, instructions, identity of the manufacturer, purpose, or characteristics of the file. A pictorial image, if provided, may convey a theme establishing a marketing identity, illustrating method of use, or merely suggesting a self-image appropriate for persuading consumers to purchase or use the file.

The file is preferably of the flexible type, so that it may conform to a finger nail or to a curved surface of any object being polished or abraded. The file is formed from a flexible synthetic resin core sandwiched by two paper or similar outer strata.

Accordingly, it is one object of the invention to provide an abrasive file which displays indicia.

A second object of the invention is to provide a mirror as part of a file.

A further object of the invention is to display indicia from a surface bearing abrasive material.

It is another object of the invention that the file be flexible.

It is a further object of the invention to convey data or information on the abrasive face of a file.

Still another object of the invention is to provide transparent or translucent abrasive material on the file.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a perspective view of one embodiment of the invention.

FIG. 2 is a perspective detail view of the embodiment of FIG. 1.

DETAILED DESCRIPTION OF THE PREFERRED EMBODIMENTS

Figure 3:
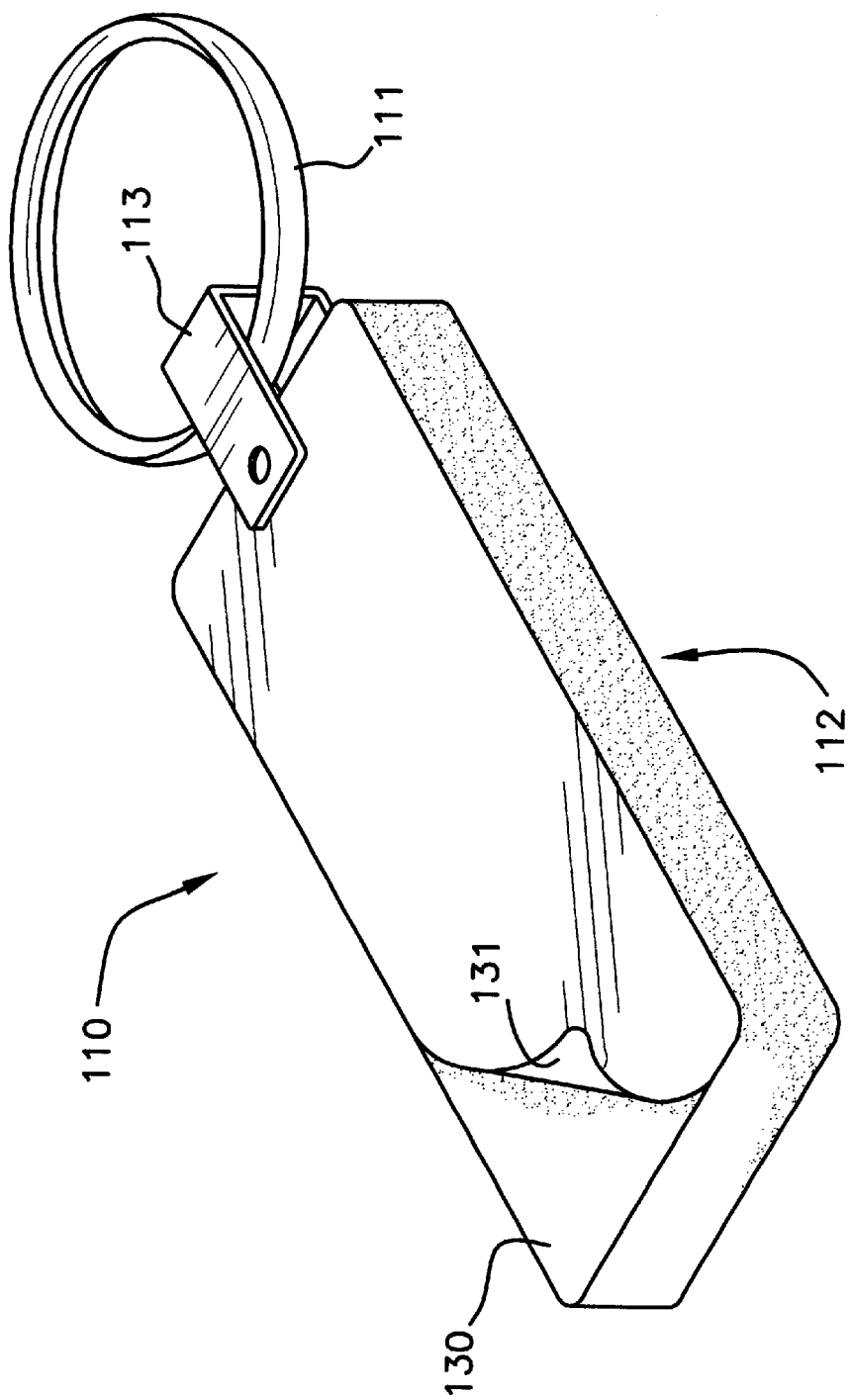
FIG. 3 is a perspective view of another embodiment of the invention.

Turning now to FIG. 1 of the drawings, file 10 is seen to comprise a generally planar body 12 having a front face 14, a rear face 16, and lateral edges 18 disposed between and spacing apart front and rear faces 14, 16. The thickness of body 12, which correlates to width of edges 18, is only nominal, in that the thickness is sufficient to impart a measure of rigidity to body 12 depending upon characteristics of the constituency of body 12.

Body 12 is partially flexible. This signifies that body 12 is sufficiently rigid to allow manual pressure to be imposed on file 10 without causing file 10 to bend to the point that it is not usable as an abrading or polishing implement. At the same time, the outer surface of body 12 can flex to a limited degree, so that faces 14, 16 are no longer planar. Rather, they become slightly curved to conform to a small extent to the surface being abraded or polished. This characteristic is useful when filing finger nails and similar curved surfaces, since it assures that contact is made on a broad area rather than at the point of tangential contact which would occur if file 10 were absolutely rigid.

Indicia 17 is disposed upon front face 16. Indicia 17 may be a pictorial image, such as a photograph, or may be printed matter. The precise nature of indicia 17 is not important, although it is preferred that indicia 17 convey information. A photograph conveys a theme which the manufacturer, seller, or user of file 10 may wish to have a consumer associate with file 10. Illustratively, when indicia 17 depicts a comely human model, a client of a beauty salon may come to associate that salon or a vendor of file 10 with a self-image promoting use of nail 10 or patronizing the salon furnishing or employing file 10. Of course, indicia 17 may contain subject matter of another type, such as instructions for use, names identifying the manufacturer or distributor of file 10, or still other information.

Indicia 17 is disposed on body 12 beneath a transparent or translucent abrasive surface. The abrasive surface is formed in any suitable way such that it both functions as an abrasive and also reveals indicia 17. Optionally, to minimize cost, the picture seen through the surface of the abrasive can be obtained by printing a reversal on the back side of the abrasive. The image then can be seen through the top surface of the abrasive eliminating the printed paper and double stick clear tape.

Clearly shown in FIG. 2, body 12 comprises a core 20 of flexible foamed synthetic resin, a first stratum 22 of bendable solid material disposed between core 20 and front face 14, and a second stratum 24 of bendable solid material disposed between core 20 and rear face 16. Constituent material of strata 22, 24 may be paper or a like material which accepts printing inks, and to which a bonding agent will bond. Indicia 17 is formed as a layer 26 of ink or inks deposited on stratum 22 of bendable material.

Abrasive surface 28 which coats front face 14 and is the outermost component of front face 14 is preferably small or finely ground grit particles embedded in a matrix including a bonding agent. It is important that the grit and bonding agent both be selected from those which are transparent or translucent, so that they enable indicia 17 to be visible or revealed through abrasive surface 28.

Stratum 30 is formed from a material displaying a mirror coating. Suitable materials for providing stratum 30 include synthetic films with or without adhesive. The mirrored coating may be non-chromatic, as is typical of silvered mirrors, or alternatively may be chromatic. If chromatic, the coating may be monochromatic or polychromatic. If polychromatic, the different hues may be in discrete zones, zones displaying gradual transition from one hue to the next, or may be arranged in the form of indicia and images. Examples of suitable films include cellulose acetate, polyester, polyvinyl chloride, as manufactured by GRAFIX Plastics, a division of GRAFIX, Inc., Cleveland, Ohio 44128.

Optionally, to reduce cost, a thicker mirror can be used in replacement of the foamed synthetic resin core 20 of FIG. 2, thereby eliminating the synthetic resin core and the double stick foam required to bond the mirror to the foamed synthetic resin.

These materials as well as those of body 12 can be formed by die cutting. Therefore, an advantageous method of fabrication includes forming body 12 and adhering stratum 30 to sheets of stock material (not shown). File 10 is formed by die cutting the stock material.

In another embodiment, shown in FIG. 3, file 110 is generally similar to the embodiment of FIG. 1, but has a ring 111 of a keychain attached thereto by engagement with a retaining strap 113. Strap 113 is attached to body 112 by a rivet 115 or other suitable fastener.

Optionally, stratum 130, which is similar to stratum 30 of the embodiment of FIG. 2, is covered by a transparent or translucent liner 131 which is dimensioned and configured to overlie stratum 130 precisely, serving as a protective covering. Liner 131 may be fabricated from a film which is retained to stratum 130 by static electrical charge, or alternatively may be coated with adhesive (not shown).

File 10 is usable in the manner of conventional finger nail files, but adds a dimension of performance by virtue of conveying the message of indicia 17 to the user and also affording the convenience of a mirror.

The present invention is susceptible to modifications and variations that may be introduced thereto without departing from the inventive concept. For example, indicia may be superimposed on the exterior of the abrasive surface of any embodiment of the invention. In still another alternative, the grit or the bonding agent or both may be impregnated with indicia. In a further alternative, the abrasive surface may be provided in a form other than that employing grit and bonding agent. For example, it may comprise a rough, open celled foam, an abraded metal substrate, or still other compositions.

Although the preferred embodiment has been described in detail, it is to be understood that the present invention is not limited to the embodiments described above, but encompasses any and all embodiments within the scope of the following claims.

I claim:

1. A file having indicia and a mirror, comprising:
   a generally planar body of nominal thickness, having a front face, a rear face, and lateral edges disposed between said front face and said rear face;
   a transparent abrasive surface disposed upon said front face, wherein said abrasive surface comprises small particles of abrasive grit and a bonding agent;
   indicia disposed upon said front face; and
   a mirror coated substrate disposed upon said rear face.

2. The file according to claim 1, wherein said generally planar body comprises a core of flexible foamed synthetic resin, a first stratum of bendable solid material disposed between said core and said front face, and a second stratum of bendable solid material disposed between said core and said rear face, said generally planar body thus being partially flexible.

3. The file according to claim 1, wherein said grit and said bonding agent are transparent, and said indicia is disposed between said body and said abrasive surface, and entirely below said abrasive surface.

4. The nail file according to claim 1, further comprising a ring of a keychain attached thereto.

5. The nail file according to claim 1, further comprising a removable liner disposed in overlying relation to said mirror coated substrate.

6. A file having revealed indicia and a mirror, comprising:
   a generally planar body of nominal thickness, having a front face, a rear face, and lateral edges disposed between said front face and said rear face, said generally planar body comprising a core of flexible foamed synthetic resin, a first stratum of bendable solid material disposed between said core and said front face, and a second stratum of bendable solid material disposed between said core and said rear face, said generally planar body thus being partially flexible;

an abrasive surface disposed upon said front face, wherein said abrasive surface comprises small particles of transparent abrasive grit and a transparent bonding agent securing said abrasive grit to said generally planar body;

indicia printed on said front face between said first stratum of bendable solid material and said abrasive surface, wherein said indicia lies entirely below said abrasive surface and is visible through said transparent abrasive grit and said transparent bonding agent; and a mirrored substrate disposed on said rear face of said body.

7. The nail file according to claim 6, further comprising a ring of a keychain attached thereto.

8. The nail file according to claim 6, further comprising a removable liner disposed in overlying relation to said mirror coated substrate.

* * * * *